United States Patent [19]

O'Lenick, Jr.

[11] Patent Number: 5,034,143
[45] Date of Patent: Jul. 23, 1991

[54] NOVEL LUBRICATING GUERBET LACTAMS

[75] Inventor: Anthony J. O'Lenick, Jr., Lilburn, Ga.

[73] Assignee: LCE Partnership, Lake Geneva, Wis.

[21] Appl. No.: 507,919

[22] Filed: Apr. 12, 1990

[51] Int. Cl.$^5$ .................. C07D 207/12; C07D 207/24; C07D 207/36; C10M 133/44
[52] U.S. Cl. ........................ 252/51.5 R; 252/51.5 A; 548/551
[58] Field of Search ..................... 252/51.5 R, 51.5 A; 548/551

[56] References Cited

U.S. PATENT DOCUMENTS

| 3,188,317 | 6/1965 | Hickner | 548/551 |
| 3,823,160 | 7/1974 | Smith | 548/551 |
| 3,853,910 | 12/1974 | Freyermuth et al. | 548/551 |
| 4,397,750 | 8/1983 | Chibnik | 252/51.5 A |
| 4,837,337 | 6/1989 | Murao et al. | 548/551 |

OTHER PUBLICATIONS

Chemical Abstract, 108(19):167333w.
Chemical Abstract, 109(11):92833u.

Primary Examiner—Prince E. Willis
Assistant Examiner—Jerry D. Johnson

[57] ABSTRACT

The present invention deals with the certain novel lactam based lubricating components which are guerbet alcohol derived ether containing lactam compounds. These materials are useful as lubricating oils where outstanding liquidity, resistance to oxidation, and minimal variation in viscosity as a function of temperature is required. This combination of properties make these compounds excellent candidates as additives to synthetic lubricating oil and extreme pressure additives.

15 Claims, No Drawings

NOVEL LUBRICATING GUERBET LACTAMS

BACKGROUND OF THE INVENTION

1. Field of the Invention

The present invention deals with the certain novel lactam based lubricating components which are guerbet alcohol derived ether containing lactam compounds. These materials are useful as lubricating oils where outstanding liquidity, resistance to oxidation, and minimal variation in viscosity as a function of temperature is required. This combination of properties make these compounds excellent candidates as additives to synthetic lubricating oil and extreme pressure additives.

2. Description of the Art Practices

Lower alkyl pyrrolidones have found applications as low toxicity aprotic solvents. However the absence of a hydrophobe on the molecule make the lower alkyl products water soluble and of no value as oil additives.

The reaction of aliphatic primary amines with butyrolactone is well known to those skilled in the art and is disclosed in various publications and a series of patents by Rajadhyaksha, including U.S. Pat. No. 4,423,040 issued Dec. 27, 1983, which teaches that 1-substituted azacyclohexan-2-ones can be prepared and used as physiologically active agents. Related patents to Rajadhyaksha include U.S. Pat. Nos. 4,525,199; 4,461,638; 4,444,762; 4,562,075; 4,316,893; 4,122,170; 4,405,616; and 4,415,563. These materials are surfactants, emulsifiers or wetting agents and lack both the ether linkage and the required guerbet moiety and consequently are of no value as synthetic lubricant additives.

U.S. Pat. No. 3,188,317 to Hickner discloses a series of products which are oxazolidinone derivatives useful as herbicides. The Hickner products while structurally related to the compounds of the present invention, lack the guerbet functionaily which is critical for the lubrication, liquidity, oxidative stability and other functional properties of the present invention. These new attributes are unexpected results which are superior to and unanticipated by Hickner. Additionally, the Hickner patent requires the reaction of the anion of the hydroxyl group of the alcohol with a halogenated intermediate. As will be shown later, guerbet alcohols, by virtue of their bulky beta branch, are not reactive with the halogenated intermediate of Hickner. In short, guerbet alcohols could not be substituted into the invention of Hickner to give the desired products.

U.S. Pat. No. 4,731,190 to O'Lenick teaches that certain alkoxylate esters are useful as lubricants useful in facilitating the working of metal. Unlike the compounds of the present invention the O'Lenick compounds are esters and as such are subject to hydrolysis if used as lubrication oils. Additionally the O'Lenick esters are also alkoxylated to make them surface active. The compounds of this invention are hydrolytically stable lactams and are not surface active.

THE INVENTION

This invention relates to a particular group of guerbet containing ether amine derived N substituted lactams and the novel properties of these materials. An additional aspect of the invention is the application of these materials as lubricating oils were (a) the specific ether linkage, (b) the guerbet structure and (c) the lactam structure all work together to give superior liquidity, lubricity and oxidative stability.

The compounds of the current invention conform to the following structure;

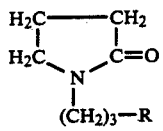

wherein R is

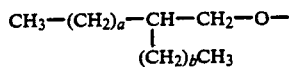

a and b are independently integers from 3 to 17 with the proviso that a+b be at least 8.

The high molecular weight, and reglospecific branched nature of the guerbet amine and the cyclic nature of these compounds, the presence of the ether linkage, and the hydrophobic nature of the "R" group taken together result in maximum efficiency as surface active agents.

In order to evaluate the utility of guerbet alcohols in amine chemistries we tried to make guerbet based amines "gurbamines" using standard chemistry, with little success.

| Route 1 Direct Ammonia reaction | | |
|---|---|---|
| Fatty Alcohol + Ammonia → Fatty Amine | | (I) |
| Starting Alcohol | % Conversion | |
| Guerbet | 15.6 | |
| Stearyl Alcohol | 96.5 | |
| Decyl Alcohol | 98.2 | |
| t-butanol | 5.0 | |

| Route 2 Alkyl Halide Reaction | | |
|---|---|---|
| Fatty Alcohol + PBr₃ → Fatty Bromide | | (II) |
| Fatty Bromide + Ammonia → Fatty Amine | | (III) |
| Starting Alcohol | % Conversion | |
| Guerbet | 21.6 | |
| Stearyl Alcohol | 97.5 | |
| Decyl Alcohol | 99.2 | |

We were unable to get the desired "gurbamine" product in any acceptable yield using the above routes, or using the process of Hickner. It was apparent that the beta branching in the guerbet was resulting in appreciable steric hindrance and consequently little reaction. This hindrance makes the conversion of a guerbet alcohol to an amine a technically unappealing and practically impossible reaction. However, as we later found out the guerbet's structural feature is of critical importance to obtain the product's performance of the compounds of the present invention. The use of the ether amine chemistry not only allowed us to prepare the desired amines in high yields but also gave the desired concentration of a highly regiospecific beta branching.

The novel lactam compounds of this invention may be prepared from guerbet alcohols having from 12 to 40 total carbon atoms by a process which includes as a first step the cyanoethylation of the guerbet alcohol with acrylonitrile in the presence of an alkaline catalyst, e.g., benzyltrimethylammonium hydroxide, potassium hydroxide, sodium methoxide, or sodium hydroxide. The guerbet alcohol and acrylonitrile may be reached at temperatures between about 25° C., and about 80° C., in the presence of about 0.1 percent potassium hydroxide for a period of about five to about six hours. The reaction is generally exothermic and external cooling may be required to prevent polymerization of the acrylonitrile. The use of an organic solvent diluent also aids in reducing acrylonitrile polymerization. A yield of between about 95 and about 100 percent is generally obtained.

The product is then hydrogenated in the presence of a suitable catalyst, e.g., Raney nickel, to form an alkoxypropylamine. The hydrogenation of the oxypropionitrile is preferably carried out at a temperature of 125° C., with a hydrogen partial pressure of about 300 psig. and in an ammonia partial pressure of 200 psig. Alternately, an ammonia partial pressure of between 0 and 300 psig. and a hydrogen partial pressure of between 200 and 600 psig. may be employed. A yield of 95 to 100 percent of alkoxypropylamine is obtained. It is also contemplated to reduce the oxypropionitrile with a suitable reducing agent, e.g., lithium aluminum hydride, to form b-alkoxypropylamine in place of the hydrogenation step.

The guerbet ether amines useful as raw materials for the preparation of the compounds of this invention are also commercially available from Tomah Products, Milton Wis.

Guerbet Alcohols are regiospecifically beta branched alcohols. They have been known since the 1890's when Marcel Guerbet first synthesized them. (M. Guerbet, C. R. Acad. Sci. Paris, 128, 511; 1002 (1899)). These materials are high in molecular weight and are liquid to very low temperatures. The guerbet reaction gives very specific branching in the alcohol as shown:

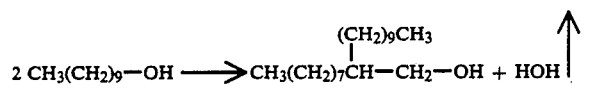

As can be seen by the above reaction the molecules have substitution on the second carbon from the hydroxyl group. This branching has been found to be critical to the preparation of a product having the desired lubrication and oxidative stability properties. If the branching were on the same carbon as the hydroxyl group, the hydroxyl group would be a secondary one and would be very hindered and has low reactivity. As one moves the branch position away from the beta carbon, the liquidity, lubricity and metal substantivity decreases. If the branch is lower alkyl like methyl in some oxo alcohols, there is little increase in the liquidity, lubricity and metal substantivity over normal alcohols having the same number of carbons. Additionally, the oxo process gives only some beta branching (between 1 and 28%) the guerbet process gives essentially 100% product.

Guerbet alcohols that are the reaction product of one specific raw material alcohol will result in a so called "homo-guerbet". In this case R and R' are identical. If the starting alcohols used in the guerbet reaction are of differing molecular weights a so called "hetero-guerbet" results. This type of guerbet has a mixed distribution of all possible combinations of alcohols. For this reason R and R' in the generic formula may be the same or different.

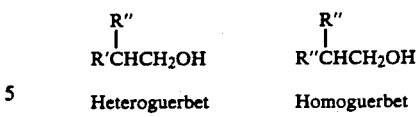

Heteroguerbet    Homoguerbet

The use of guerbet derived ether amines to prepare compounds of this invention results in substantive liquid products. The high molecular weight of the hydrophobe results in liquid oil phases that have outstanding lubricity.

EXAMPLES

For comparison, a non guerbet derived product based upon a stearic ether amine (example A) and a non ether linear product (Example B) was prepared and evaluated. Both materials are a waxy solid.

EXAMPLE A

Into a stainless autoclave was introduced 298.0 grams of $CH_3—(CH_2)_{17}—O—(CH_2)_3—NH_2$ and 95.0 grams of butyrolactone. The autoclave was sealed and 100 psig nitrogen was applied. The contents were heated to 275° C. and held for eight hours, during which time the pressure rose to about 480 psig. The reaction product was distilled to give a product which conformed to the following generic structure;

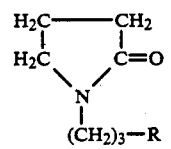

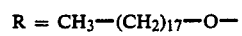

$R = CH_3—(CH_2)_{17}—O—$

EXAMPLE B

Into a stainless autoclave was introduced 240.0 grams of $CH_3—(CH_2)_{17}—NH$ and 95.0 grams of butyrolactone. The autoclave was sealed and 100 psig nitrogen was applied. The contents were heated to 275° C. and held for eight hours, during which time the pressure rose to about 480 psig. The reaction product was distilled to give a product which conformed to the following generic structure;

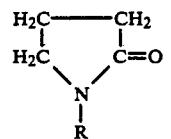

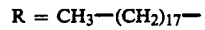

$R = CH_3—(CH_2)_{17}—$

The following are suggested embodiments of present invention.

GENERAL PROCEDURE

Into a stainless autoclave was introduced the specified amount of the specified guerbet alcohol derived ether amine and 95.0 grams of butyrolactone. The autoclave was sealed and 100 psig nitrogen was applied. The contents were heated to 275° C. and held for eight hours, during which time the pressure rose to about 480 psig. The reaction product was distilled to give a product which conformed to the following generic structure;

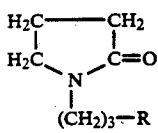

wherein R is

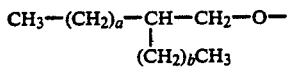

The ether amines were prepared by Tomah Products Milton Wis. and conform to the following structures;

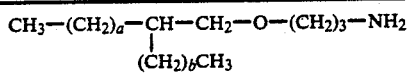

| Example | a | b | Grams |
|---------|----|----|-------|
| 1 | 7 | 9 | 355.0 |
| 2 | 3 | 5 | 243.0 |
| 3 | 10 | 12 | 395.0 |
| 4 | 15 | 17 | 579.0 |
| 5 | 3 | 17 | 371.0 |
| 6 | 17 | 17 | 539.0 |
| 7 | 5 | 3 | 243.0 |

APPLICATIONS EXAMPLES

Lubrication Testing

The compounds of the present invention were evaluated using a standard Rothchild Tester to determine the lubrication properties. The values below indicate the lubricating efficiencies of various standard type lubricants, a non guerbet product and a product which is non guerbet derived made using the technology described in the patent of Hickner. The lower the frictional value the better the lubricating properties.

| | FRICTIONAL PROPERTIES | | |
|---|---|---|---|
| | | LUBRICATION DATA* Coefficient of Friction FIBER/METAL | |
| PRODUCT | DESCRIPTION (22 C.) | 100 (m/min) | 300 (m/min) |
| Example 1 | Clear oil | 0.25 | 0.26 |
| Example 2 | Clear Yellow liquid | 0.26 | 0.30 |
| Example 4 | Clear Oil | 0.22 | 0.24 |
| Example 6 | Clear Oil | 0.22 | 0.24 |
| Polyethyleneglycol tall oil Ester | Hazy Oil | 0.38 | 0.35 |
| TMP Trioleate | Clear Amber Liquid | 0.35 | 0.39 |
| Stearic Ether Lactam (Example # A) | White Solid | 0.45 | 0.48 |
| Stearic Lactam (Example # B) | White Solid | 0.48 | 0.53 |

*Rothchild F Meter, Fiber; 150 denier polyester, Temperature: 72° F., Relative humidity: 60%

As can be easily seen the compounds of the present invention are good lubricants for fiber to metal lubrication.

The additives of the present invention were formulated with a commercially available base fluid and tested in a four ball tester apparatus according to the test procedure ANSI/ASTM D-2266-67 and ANSI/ASTM D-2783-71 to determine antiwear and extreme pressure properties.

1% of the experimental compound was added to the base fluid (SUNVIS 31) under good agitation. The solutions were tested in a four ball tester at 40 kg load weight and 1,800 rpm at 170° F. The results are as follows;

| Four Ball Antiwear Testing | | |
|---|---|---|
| Load Carrying Additive | Base Fluid | Average Scar Diameter (mm) |
| None | SUNVIS 31 | 0.63 |
| Example 1 | SUNVIS 31 | 0.47 |
| Example 2 | SUNVIS 31 | 0.41 |
| Example 4 | SUNVIS 31 | 0.43 |
| Example 6 | SUNVIS 31 | 0.40 |
| Example A (Non Guerbet) | SUNVIS 31 | 0.62 |
| Example B (Non ether non guerbet) | SUNVIS 31 | 0.64 |

As can be seen from the data the compounds of the present invention are good lubricants. The nonguerbet product was a poor additive.

| | Four Ball Extreme Pressure Test | | |
|---|---|---|---|
| Load Carrying Additive | Base Fluid | Load Wear Index | Last Nonseizure | Weld Load |
| None | SUNVIS 31 | 14 | 32 | 160 |
| Example 1 | SUNVIS 31 | 25 | 51 | 200 |
| Example 2 | SUNVIS 31 | 28 | 53 | 210 |
| Example 4 | SUNVIS 31 | 26 | 51 | 225 |
| Example 6 | SUNVIS 31 | 25 | 50 | 230 |
| Example A (Non Guerbet) | SUNVIS 31 | 15 | 33 | 175 |
| Example B (Non Guerbet) | SUNVIS 31 | 14 | 36 | 180 |

SUNVIS 31 is a high viscosity index, neutral petroleum oil of parafinnic base.

As can be seen from the data the compounds of the present invention are good lubricants. The nonguerbet product was a poor additive.

We have therefore shown that the following functional attributes need to be present in the molecules of the present invention to result in the performance properties;

1. The guerbet branching—The linear product based upon a stearyl ether amine does not function well.

2. The ether function—The preparation of a guerbet amine was found to be technically impossible. The reaction of the hindered hydroxyl group results in the desired product.

3. The three methylene groups between the ether oxygen and the guerbet—This is a consequence of the need to use acrylonitrile to make the desired product. Acrylonitrile is reactive by the alpha beta structure and for this reason has three carbon atoms and only three carbon atoms.

highly reactive structure.

What is claimed is:

1. A substituted lactam conforming to the following formula;

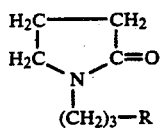

wherein;
R is;

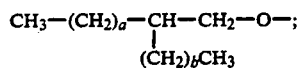

a and b are independently integers from 3 to 17 with the proviso that a+b be at least 8.

2. A compound of claim 1 wherein the sum of a and b is 16.

3. A compound of claim 1 wherein the sum of a and b is 8.

4. A compound of claim 1 wherein the sum of a and b is 22.

5. A compound of claim 1 wherein the sum of a and b is 34.

6. A compound of claim 1 wherein the sum of a and b is 20.

7. A lubricating composition comprising a lubricating base oil and an effective lubricating amount of a substituted lactam conforming to the following formula;

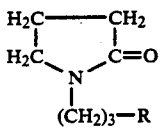

wherein;
R is;

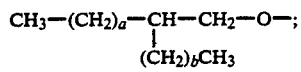

a and b are independently integers from 3 to 17 with the proviso that a+b be at least 8.

8. A composition of claim 7 wherein the sum of a and b in the substituted lactam is 16.

9. A composition of claim 7 wherein the sum of a and b in the substituted lactam is 8.

10. A composition of claim 7 wherein the sum of a and b in the substituted lactam is 22.

11. A composition of claim 7 wherein the sum of a and b in the substituted lactam is 34.

12. A composition of claim 7 wherein the sum of a and b in the substituted lactam is 20.

13. A composition of claim 7 wherein the effective lubricating amount ranges from 0.2 to 50% by weight.

14. A composition of claim 7 wherein the concentration of lactam ranges from 1.0 to 5.0% by weight.

15. A composition of claim 7 wherein the concentration of lactam ranges from 0.2 to 3.0% by weight.

* * * * *